(12) United States Patent
Meier et al.

(10) Patent No.: US 8,750,546 B2
(45) Date of Patent: Jun. 10, 2014

(54) SOUND PROCESSORS AND IMPLANTABLE COCHLEAR STIMULATION SYSTEMS INCLUDING THE SAME

(75) Inventors: Roger S. Meier, Canyon Country, CA (US); Lee F. Hartley, Valencia, CA (US); James P. Goodman, Valencia, CA (US)

(73) Assignee: Advanced Bionics, Valencia, CA (US)

( * ) Notice: Subject to any disclaimer, the term of this patent is extended or adjusted under 35 U.S.C. 154(b) by 0 days.

(21) Appl. No.: 12/972,349

(22) Filed: Dec. 17, 2010

(65) Prior Publication Data

US 2011/0103627 A1    May 5, 2011

Related U.S. Application Data

(63) Continuation-in-part of application No. 12/568,851, filed on Sep. 29, 2009, now Pat. No. 8,437,860.

(60) Provisional application No. 61/102,726, filed on Oct. 3, 2008.

(51) Int. Cl.
*H04R 25/00* (2006.01)
*A61N 1/36* (2006.01)

(52) U.S. Cl.
CPC .............. *H04R 25/00* (2013.01); *H04R 25/556* (2013.01); *H04R 25/60* (2013.01); *A61N 1/36032* (2013.01)
USPC ............ 381/323; 381/322; 381/326; 439/188

(58) Field of Classification Search
CPC ...... H04R 25/00; H04R 25/556; H04R 25/60; A61N 1/36032
USPC ........... 381/314, 322, 323, 324, 326; 439/188
See application file for complete search history.

(56) References Cited

U.S. PATENT DOCUMENTS

| | | | |
|---|---|---|---|
| 4,315,111 A | 2/1982 | Thomas | |
| 4,467,145 A | 8/1984 | Borstel | |
| 4,578,628 A * | 3/1986 | Siwiak | .......................... 320/127 |
| 4,751,485 A | 6/1988 | Fujio et al. | |
| 4,879,443 A | 11/1989 | Carlucci et al. | |
| 4,918,737 A | 4/1990 | Luethi | |
| 5,553,152 A | 9/1996 | Newton | |
| 5,659,621 A | 8/1997 | Newton | |
| 5,824,022 A | 10/1998 | Zilberman et al. | |
| 5,945,929 A | 8/1999 | Westra | |
| 5,948,006 A | 9/1999 | Mann | |
| 6,269,266 B1 | 7/2001 | Leysieffer | |

(Continued)

FOREIGN PATENT DOCUMENTS

| | | |
|---|---|---|
| DE | 3723809 A1 | 1/1989 |
| DE | 10228828 C1 | 10/2003 |

(Continued)

OTHER PUBLICATIONS

Office Action dated Jun. 5, 2012 in U.S. Appl. No. 12/568,851.

(Continued)

*Primary Examiner* — Curtis Kuntz
*Assistant Examiner* — Ryan Robinson
(74) *Attorney, Agent, or Firm* — Henricks, Slavin & Holmes LLP

(57) ABSTRACT

Sound processors and systems including sound processors are disclosed.

23 Claims, 11 Drawing Sheets

(56) References Cited

U.S. PATENT DOCUMENTS

| | | |
|---|---|---|
| 6,272,382 B1 | 8/2001 | Faltys |
| 6,818,845 B2 | 11/2004 | Portmann |
| 6,831,988 B2 * | 12/2004 | Vonlanthen .................. 381/323 |
| 7,003,876 B2 | 2/2006 | Crawford et al. |
| 7,012,200 B2 | 3/2006 | Moller |
| 7,016,511 B1 | 3/2006 | Shennib |
| 7,069,063 B2 | 6/2006 | Halkosaari et al. |
| 7,117,286 B2 * | 10/2006 | Falcon .......................... 710/303 |
| 7,194,101 B2 * | 3/2007 | Vonlanthen .................. 381/322 |
| 7,248,712 B2 | 7/2007 | Gabathuler |
| 7,260,232 B2 | 8/2007 | Shennib |
| D560,808 S | 1/2008 | Jurkiewicz |
| 7,349,741 B2 | 3/2008 | Maltan et al. |
| 7,394,911 B2 | 7/2008 | Joergensen et al. |
| 7,440,579 B2 | 10/2008 | Vonlanthen |
| 7,450,732 B2 * | 11/2008 | Kragelund .................... 381/323 |
| 7,477,753 B2 | 1/2009 | Buckley et al. |
| 7,529,587 B2 | 5/2009 | Single |
| 7,566,296 B2 | 7/2009 | Zimmerling et al. |
| 7,578,628 B2 * | 8/2009 | Sherman et al. ................ 400/88 |
| 7,602,929 B2 * | 10/2009 | Topholm et al. ............. 381/322 |
| 7,660,633 B2 * | 2/2010 | Darley et al. .................. 607/57 |
| 7,729,774 B1 | 6/2010 | Lynch et al. |
| 7,751,898 B2 | 7/2010 | Ibrahim et al. |
| 8,352,037 B2 | 1/2013 | Darley et al. |
| 8,437,860 B1 | 5/2013 | Crawford et al. |
| 2001/0046808 A1 | 11/2001 | Jorgensen et al. |
| 2003/0057075 A1 | 3/2003 | Portmann |
| 2004/0012470 A1 | 1/2004 | Zimmerling et al. |
| 2004/0052388 A1 | 3/2004 | Niederdrank |
| 2004/0073275 A1 * | 4/2004 | Maltan et al. .................... 607/57 |
| 2004/0159535 A1 | 8/2004 | Wagner |
| 2004/0252855 A1 | 12/2004 | Vasserman et al. |
| 2005/0008178 A1 | 1/2005 | Joergensen |
| 2006/0126876 A1 | 6/2006 | Shennib |
| 2007/0127757 A2 | 6/2007 | Darbut et al. |
| 2007/0154042 A1 | 7/2007 | Buckley et al. |
| 2007/0171013 A1 | 7/2007 | Fujimori et al. |
| 2007/0253584 A1 | 11/2007 | Rass |
| 2008/0060917 A1 | 3/2008 | Chia-Li et al. |
| 2008/0232623 A1 * | 9/2008 | Solum et al. .................. 381/323 |
| 2008/0288022 A1 * | 11/2008 | Van der Borght et al. ...... 607/57 |
| 2009/0123013 A1 | 5/2009 | Leong |
| 2009/0239135 A1 | 9/2009 | Wang et al. |
| 2009/0325046 A1 | 12/2009 | Yang |
| 2010/0032267 A1 | 2/2010 | Gabathuler et al. |
| 2010/0260367 A1 | 10/2010 | Hasler et al. |

FOREIGN PATENT DOCUMENTS

| | | |
|---|---|---|
| EP | 0573471 B1 | 10/1994 |
| EP | 0982784 B1 | 4/2002 |
| EP | 0779015 B1 | 7/2002 |
| EP | 1271898 B1 | 1/2003 |
| EP | 1496530 B2 | 10/2006 |
| GB | 2133133 A | 7/1984 |
| JP | 05002960 A | 1/1993 |
| JP | 2003210395 A | 7/2003 |
| JP | 2009021910 A2 | 1/2009 |
| WO | WO 9216002 A1 | 9/1992 |
| WO | WO 9607295 A1 | 3/1996 |
| WO | WO-9850281 | 11/1998 |
| WO | WO 2004050166 A1 | 6/2004 |
| WO | WO 2005048474 A1 | 5/2005 |
| WO | WO 2005062668 A1 | 7/2005 |
| WO | WO-2006071210 A1 | 7/2006 |
| WO | WO 2007117721 | 10/2007 |
| WO | WO 2009118047 | 10/2009 |
| WO | WO 2009127745 | 10/2009 |

OTHER PUBLICATIONS

Office Action dated Oct. 25, 2012 in U.S. Appl. No. 12/568,851.
U.S. Appl. No. 12/568,851, filed Sep. 29, 2009, Inventors Lee Hartley and Scott Crawford.

* cited by examiner

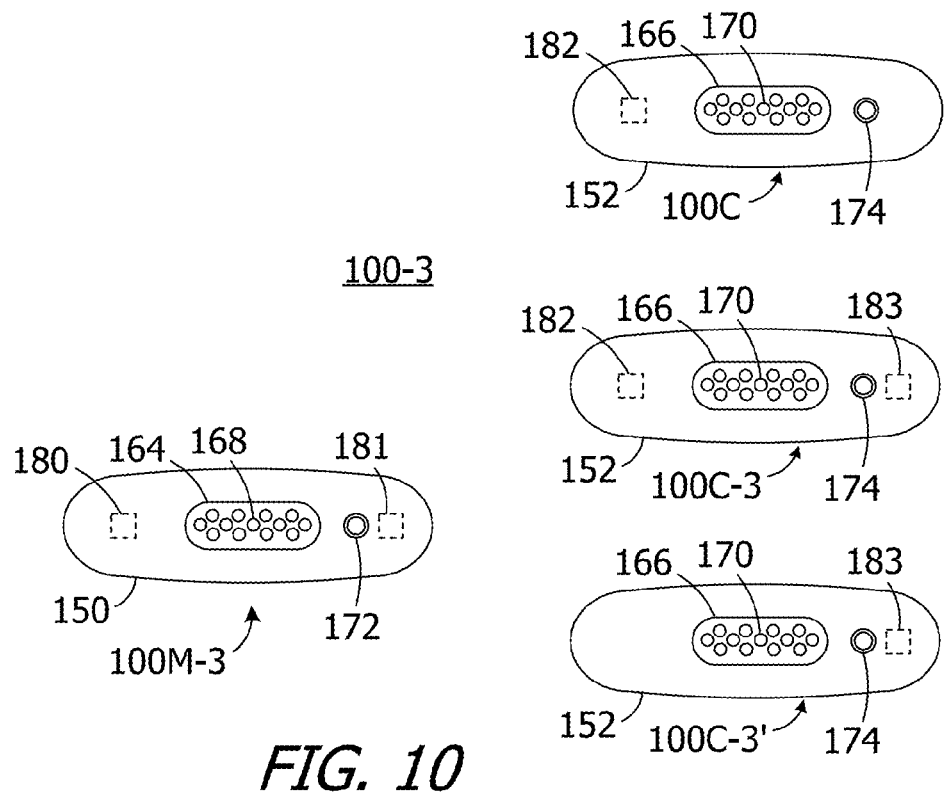
FIG. 10
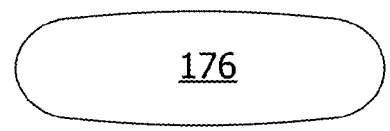
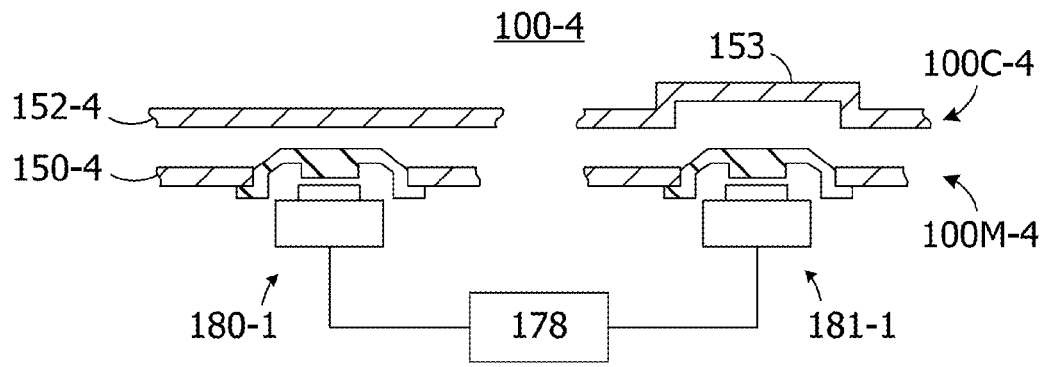
FIG. 10A

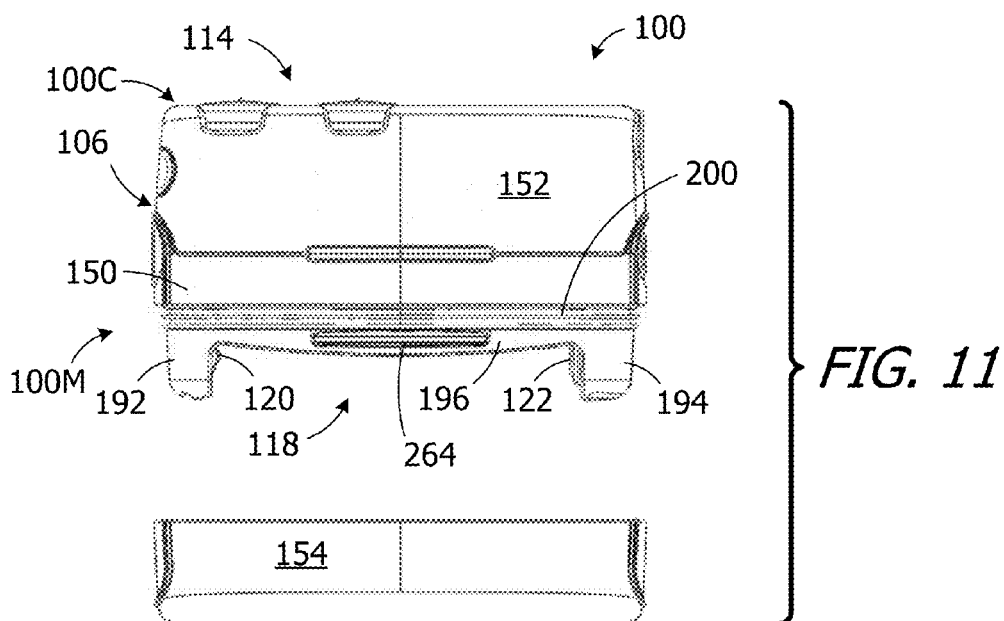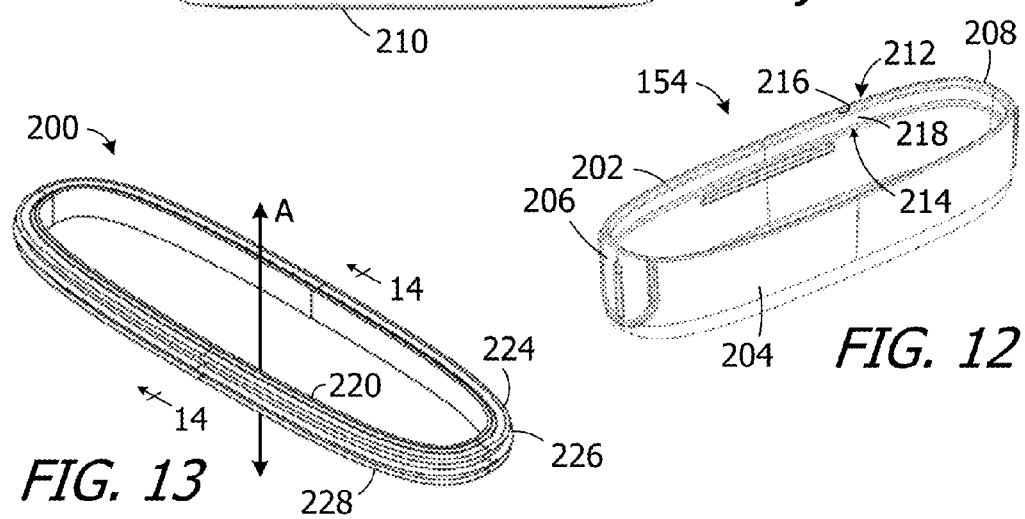

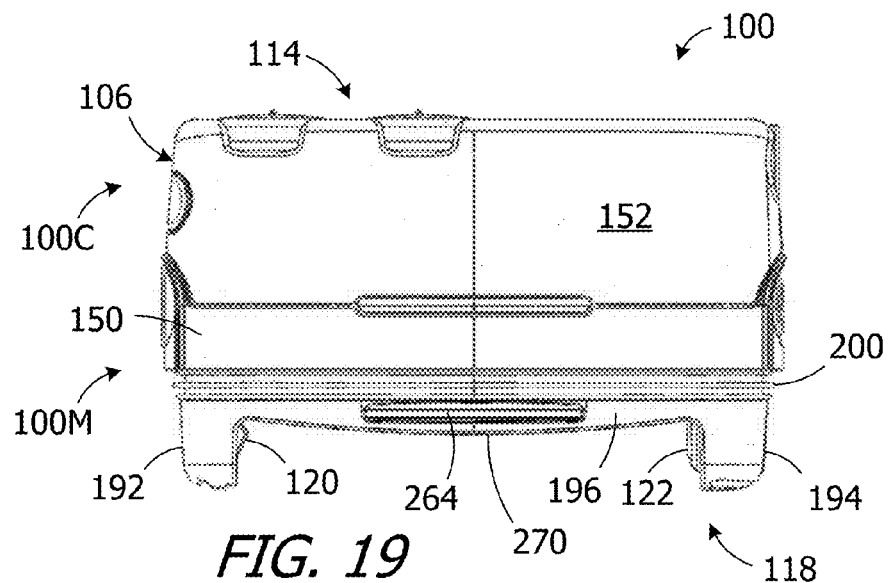
FIG. 19
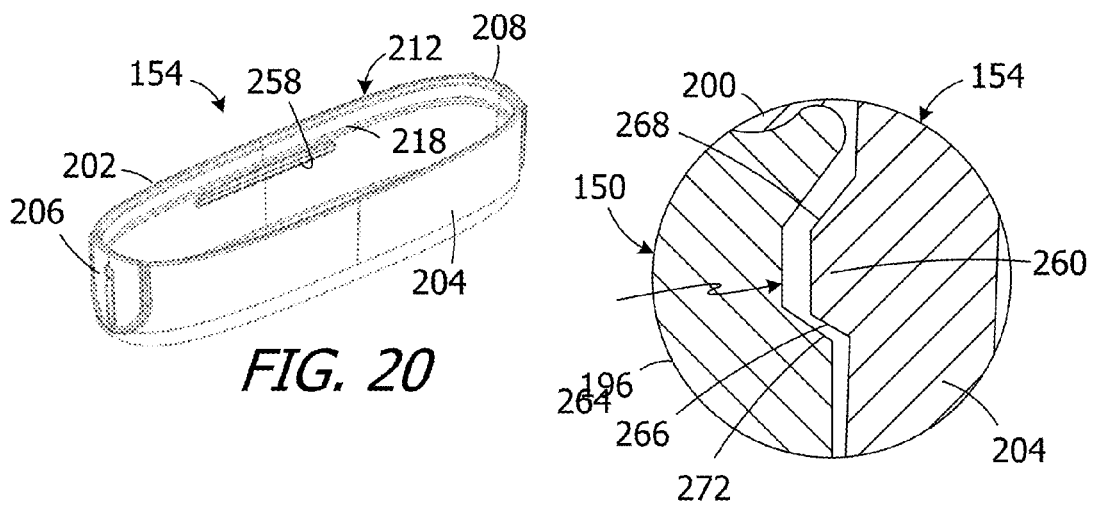
FIG. 20
FIG. 22
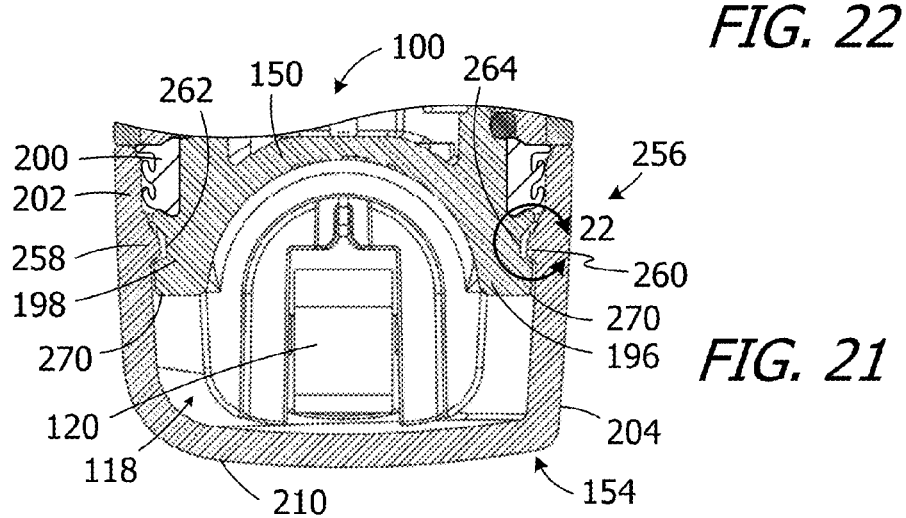
FIG. 21

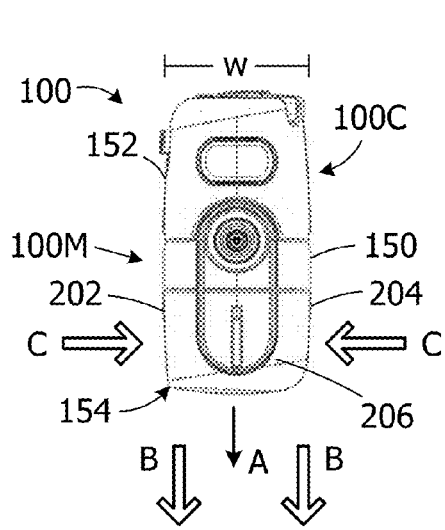
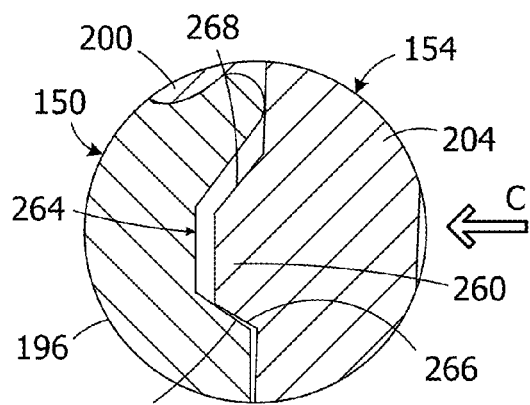
FIG. 23
FIG. 24
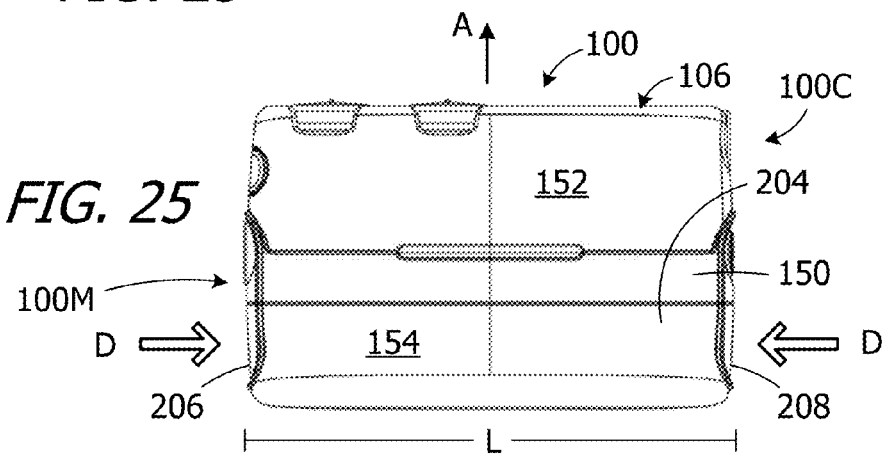
FIG. 25
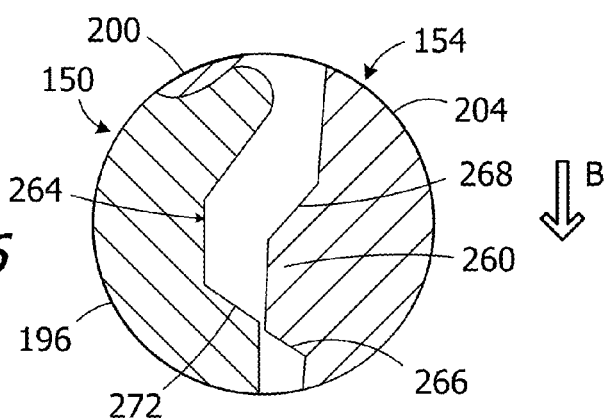
FIG. 26

SOUND PROCESSORS AND IMPLANTABLE COCHLEAR STIMULATION SYSTEMS INCLUDING THE SAME

CROSS-REFERENCE TO RELATED APPLICATIONS

This application is a continuation-in-part of U.S. application Ser. No. 12/568,851, filed Sep. 29, 2009, now U.S. Pat. No. 8,437,860 which claims benefit of U.S. Prov. App. Ser. No. 61/102,726, filed Oct. 3, 2008.

BACKGROUND

1. Field

The present disclosure relates generally to sound processors such as, for example, the sound processors in implantable cochlear stimulation (or "ICS") systems.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. A representative ICS system is disclosed in U.S. Pat. No. 5,824,022, which is entitled "Cochlear Stimulation System Employing Behind-The-Ear Sound processor With Remote Control" and incorporated herein by reference in its entirety.

As alluded to above, some ICS systems include an implantable device, a sound processor with sound processing circuitry, and a microphone that is in communication with the sound processor. The implantable device communicates with the sound processor and, to that end, some ICS systems include a headpiece that is in communication with both the sound processor and the implantable device. In one type of ICS system, the sound processor is worn behind the ear (or "BTE") sound processor, while other types of ICS systems have a body worn sound processor. The body worn sound processor, which is larger and heavier than a BTE sound processor, is typically worn on the user's belt or carried in the user's pocket. One example of a conventional body worn sound processor is the Advanced Bionics Platinum Series body worn sound processor.

Sound processors can include various control structures (e.g. a volume knob and/or a program selector switch) that are typically used infrequently and can be the source of leaks should the sound processor be exposed to liquid. One possible solution is to provide a sound processor with a main portion, which includes the sound processor circuitry, and a removable control device that can be mechanically and electrically connected (or "docked") to the main portion as necessary. The electrical connector on the main portion may be configured to continuously source power so that power will be provided to the control portion when the control portion is docked. The main portion may be sealed to prevent leaks, and the control portion may be removed in those instances where the user anticipates that the sound processor will be exposed to liquid.

SUMMARY

A sound processor in accordance with at least one of the present inventions includes a dockable device including at least one dockable device electrical contact, and a main portion including at least one main portion electrical contact and a control apparatus configured to supply power to the at least one main portion electrical contact when the dockable device is docked to the main portion and to not supply power to the at least one main portion electrical contact when the dockable device is not docked to the main portion. The present inventions also include cochlear stimulation systems with such a sound processor.

A sound processor in accordance with at least one of the present inventions includes a dockable device including at least one dockable device electrical contact, a main portion at least one main portion electrical contact and means for connecting the at least one main portion electrical contact to a power source when the dockable device is docked to the main portion and disconnecting the at least one main portion electrical contact from the power source when the dockable device is not docked to the main portion. The present inventions also include cochlear stimulation systems with such a sound processor.

A method in accordance with at least one of the present inventions includes the steps of connecting a main portion electrical connector to a source of electrical power in response to a dockable device being docked to the main portion and disconnecting the main portion electrical connector from the source of electrical power in response to the dockable device being undocked from the main portion.

Such sound processors and methods are advantageous for a variety of reasons. For example, the present inventors have determined that continuously supplying power to the electrical contacts can increase the likelihood of contact corrosion in those instances where the contacts may be exposed to corrosive substances (e.g., water, salts and certain chemicals). The power supplies electromotive force that drives corrosion. Given that there is no reason to supply power to the electrical contacts when the dockable device in not docked to the main portion and that the electrical contacts are more likely to be exposed to corrosive substances when the dockable device has been removed, selectively supplying power to the contacts reduces the likelihood of corrosion without degrading the overall functionality of the sound processor.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

FIG. 10 is a plan of a sound processor main portion and various dockable devices that can be docked thereto in accordance with one embodiment of a present invention.

FIG. 10A is a section view of a portion of a sound processor in accordance with one embodiment of a present invention.

FIG. 11 is an exploded side view of a sound processor in accordance with one embodiment of a present invention.

FIG. 12 is a perspective view of a power supply receptacle cover in accordance with one embodiment of a present invention.

FIG. 13 is a perspective view of a seal in accordance with one embodiment of a present invention.

FIG. 14 is a section view taken along line 14-14 in FIG. 13.

FIG. 19 is a side view of a sound processor in accordance with one embodiment of a present invention with the power supply receptacle cover removed.

FIG. 20 is a perspective view of a power supply receptacle cover in accordance with one embodiment of a present invention.

FIG. 21 is a section view of a portion of a sound processor in accordance with one embodiment of a present invention with the power supply receptacle cover in place.

FIG. 22 is an enlarged view of a portion of FIG. 21.

FIG. 23 is an end view of a sound processor in accordance with one embodiment of a present invention.

FIG. 24 is a section view of a portion of the sound processor illustrated in FIG. 23.

FIG. 25 is a side view of a sound processor in accordance with one embodiment of a present invention.

FIG. 26 is a section view of a portion of the sound processor illustrated in FIG. 25 after slight movement from the location illustrated in FIG. 25.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

The present inventions have application in a wide variety of systems that provide sound (i.e. either sound or a perception of sound) to the hearing impaired as well as others who require such systems on a situational basis. One example of such a system is an ICS system where an external body worn sound processor communicates with a cochlear implant and, accordingly, the present inventions are discussed in the context of such ICS systems. The present inventions are not, however, limited to ICS systems and may be used in combination with other systems for the hearing impaired that currently exist, or are yet to be developed. Nor are the present inventions limited to ICS systems with body worn sound processors. The present inventions are also applicable to, for example, ICS systems with BTE sound processors.

Figure 1:
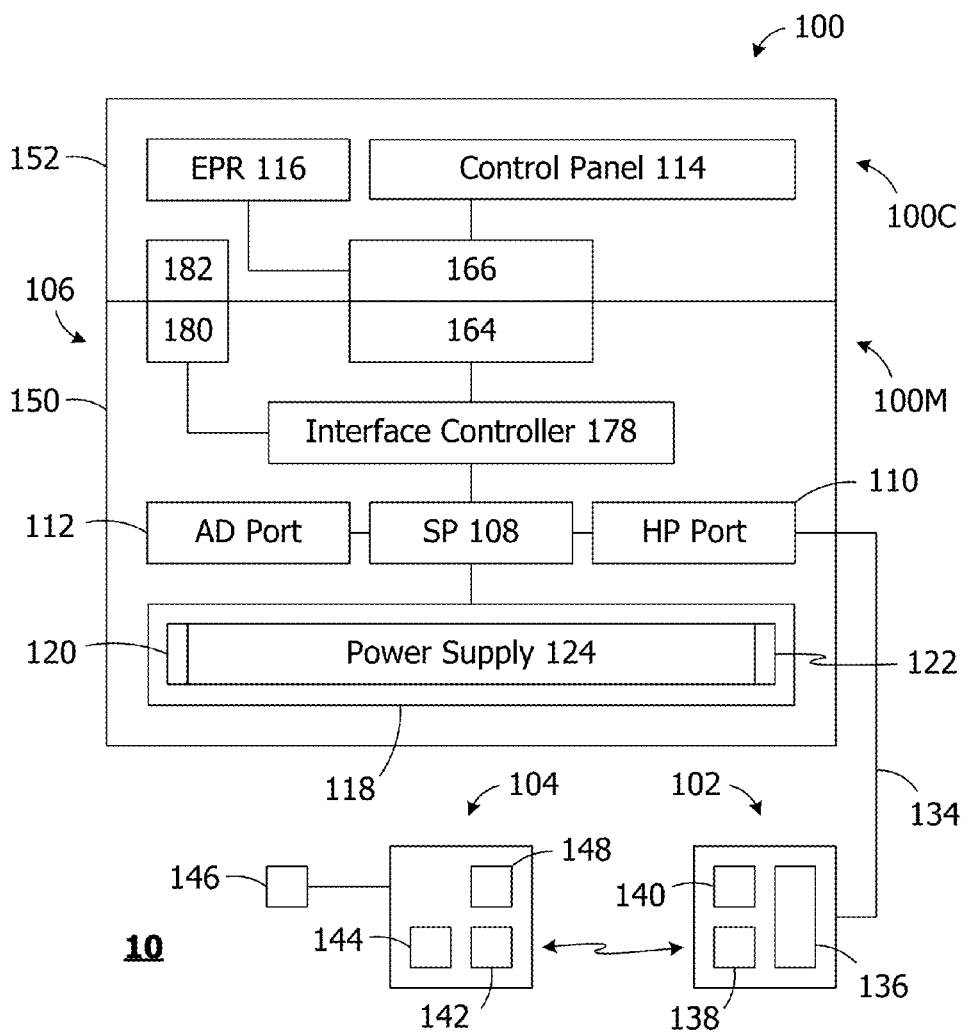
FIG. 1 is a functional block diagram of an ICS system in accordance with one embodiment of a present invention.
Figure 2:
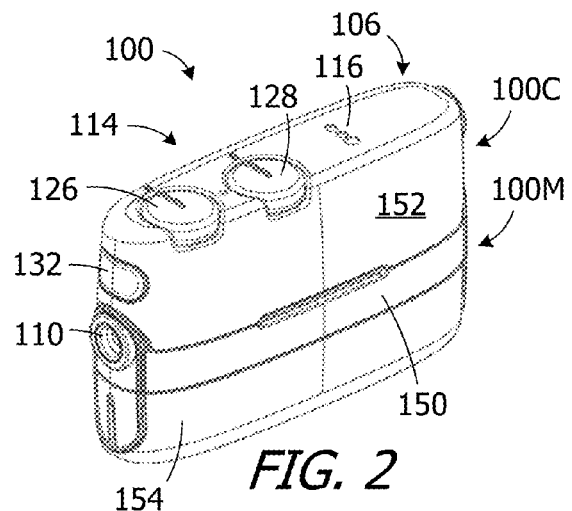
FIG. 2 is a perspective view of a sound processor in accordance with one embodiment of a present invention.
Figure 3:
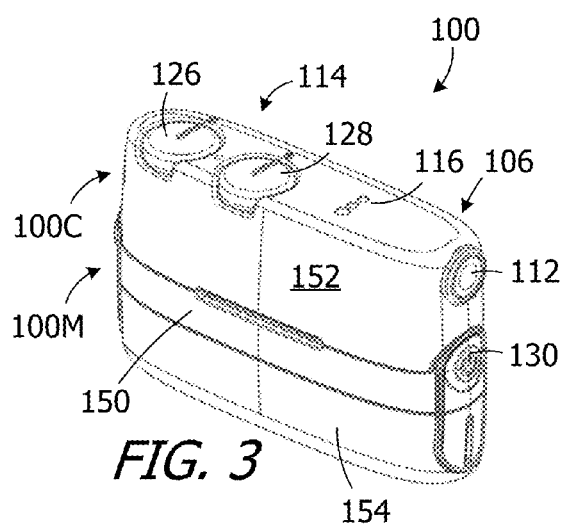
FIG. 3 is a perspective view of a sound processor in accordance with one embodiment of a present invention.

One example of a sound processor is the body worn sound processor generally represented by reference numeral 100 in FIGS. 1-3. The exemplary sound processor 100, which may be combined with a headpiece 102 and a cochlear implant 104 to form an ICS system 10, includes a housing 106 in which and/or on which various components are supported. Such components may include, but are not limited to, sound processor circuitry 108 (e.g., a microprocessor and memory) that converts sound to pulse sequences and performs the other control functions, a headpiece port 110, an auxiliary device port 112 for an auxiliary device such as a mobile phone or a music player, a control panel 114, a Euro Plug receptacle 116 (for a Euro Plug such as that associated with the Phonak MLxi FM receiver), and a power supply receptacle 118 with electrical contacts 120 and 122 for a removable battery or other removable power supply 124 (e.g. rechargeable and disposable batteries or other electrochemical cells). As discussed below, a rechargeable battery may be permanently carried within the sound processor in other embodiments.

The headpiece port 110 and auxiliary device port 112 may be connected to the sound processor circuitry 108 by way of, for example, a signal splitter/combiner (not shown) such as that found in the Platinum Signal Processor body worn unit from Advanced Bionics Corporation. In the illustrated embodiment, the control panel 114 includes a volume knob 126 and a program switch 128 (FIGS. 2-3). A power button 130 and a bayonet release button 132 are also carried on the housing 106. The bayonet release button 132 actuates a bayonet mechanism to release the control portion 100C or other dockable device from the main portion 100M (which are described below).

The headpiece 102 in the exemplary ICS system 10 (FIG. 1) includes a cable 134 which may be connected to the headpiece port 110, a microphone 136, an antenna 138 and a positioning magnet 140. The exemplary cochlear implant 104 includes an antenna 142, an internal processor 144, a cochlear lead 146 with an electrode array, and a positioning magnet (or magnetic material) 148. The transmitter 138 and receiver 142 communicate by way of electromagnetic induction, radio frequencies, or any other wireless communication technology. The positioning magnet 140 and positioning magnet (or magnetic material) 148 position the headpiece antenna 138 over the cochlear implant antenna 142. During use, the microphone 136 picks up sound from the environment and converts it into electrical impulses, and the sound processor 100 filters and manipulates the electrical impulses and sends the processed electrical signals through the cable 134 to the transmitter 138. Electrical impulses received from an auxiliary device are processed in essentially the same way. The receiver 142 receives signals from the transmitter 138 and sends the signals to the cochlear implant internal processor 144, which modifies the signals and passes them through the cochlear lead 146 to the electrode array. The electrode array may be wound through the cochlea and provides direct electrical stimulation to the auditory nerves inside the cochlea. This provides the user with sensory input that is a representation of external sound waves which were sensed by the microphone 136.

It should be noted that, in other implementations, communication between the sound processor and a headpiece and/or auxiliary device may be accomplished through wireless communication techniques. It should also be noted that, in other implementations, the sound processor may be configured to directly communicate with the cochlear implant (i.e. without a headpiece and associated cable).

The exemplary sound processor 100 may be carried by the user in a variety of ways. By way of example, but not limitation, the sound processor 100 may be carried in the user's pocket, secured to a belt with a belt clip that is either part of housing 106 or a separate carrier, or placed in a harness that is configured to be worn by a small child.

Referring more specifically to FIGS. 2 and 3, the sound processor 100 includes a sound processor main portion (or "main portion") 100M and a sound processor control portion (or "control portion") 100C that may be docked to the main portion. The main portion 100M includes the sound processor circuitry 108, headpiece port 110, power supply receptacle 118, and power button 130 as well as a main portion housing 150 for supporting and/or housing these components. A power supply receptacle cover ("PSR cover") 154 may be detachably connected to the main portion housing 150 in those instances where replaceable batteries are employed. In those instances where a permanent rechargeable battery is employed, the PSR cover 154 may be omitted and the main portion housing configured to permanently enclose the battery. The control portion 100C includes the auxiliary device port 112, control panel 114, Euro Plug receptacle 116 and bayonet release button 132 and well as the control portion housing 152 for supporting and/or housing these components. In other words, the main portion 100M includes those elements of the sound processor 100 that are required for the ICS system 10 to function (e.g., sound processor circuitry), while the control portion 100C includes various elements that are only required from time to time (e.g., the volume knob 126) or are merely useful options (e.g., the auxiliary device port 112).

Figure 4:
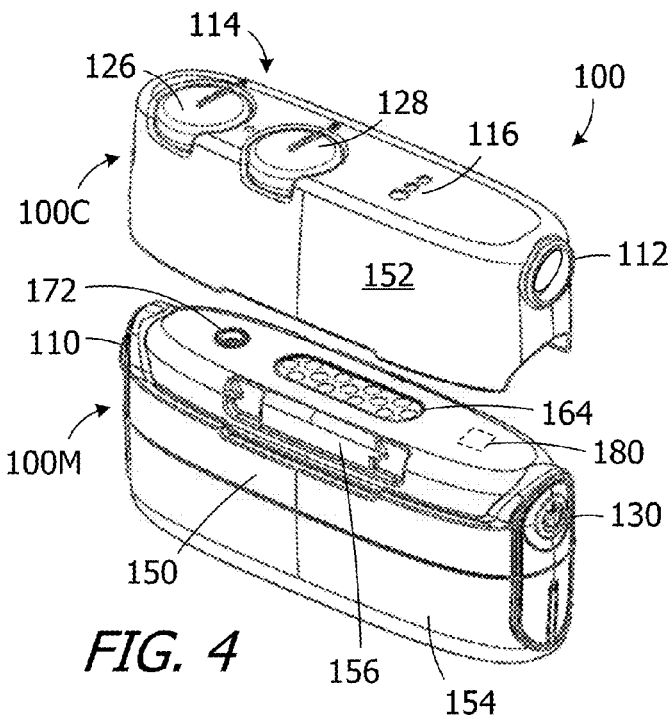
FIG. 4 is an exploded perspective view of a sound processor in accordance with one embodiment of a present invention.
Figure 7:
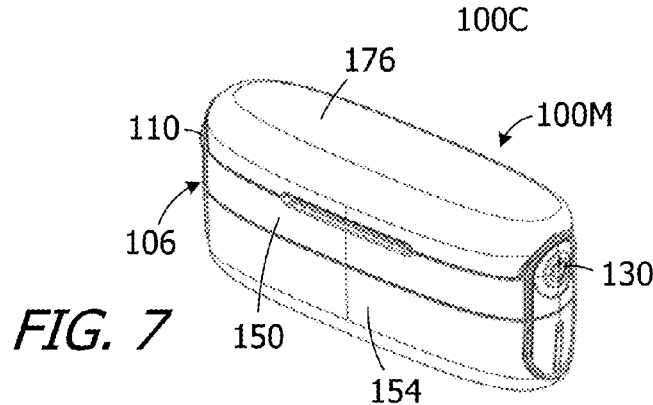
FIG. 7 is a perspective view of a sound processor in accordance with one embodiment of a present invention.

With respect to docking, the sound processor 100 is configured such that the control portion 100C (and the functional elements associated therewith) may be mechanically and electrically separated from the main portion 100M (and the functional elements associated therewith) in the manner illustrated in FIG. 4. To that end, and referring also to FIGS. 5 and 6, the exemplary main portion housing 150 may include mechanical connectors 156 and 158 that are configured to mate with corresponding connectors 160 and 162 on the control portion housing 152. The main portion 100M and control portion 100C also include electrical connectors 164 and 166 with respective pluralities of electrical contacts 168 and 170. The electrical contacts 168 and 170 may be in the form of pins, pads or any other suitable device. An alignment locater feature, such as a post 172 and an opening 174 that receives the post and keys orientation, is also provided. Turning to FIG. 7, the sound processor 100 may also include a cover 176, with the same mechanical connectors (not shown) as the control portion housing 152, that may be used to protect the electrical connector 164 when the control portion is not in use.

Figures 5, 6:
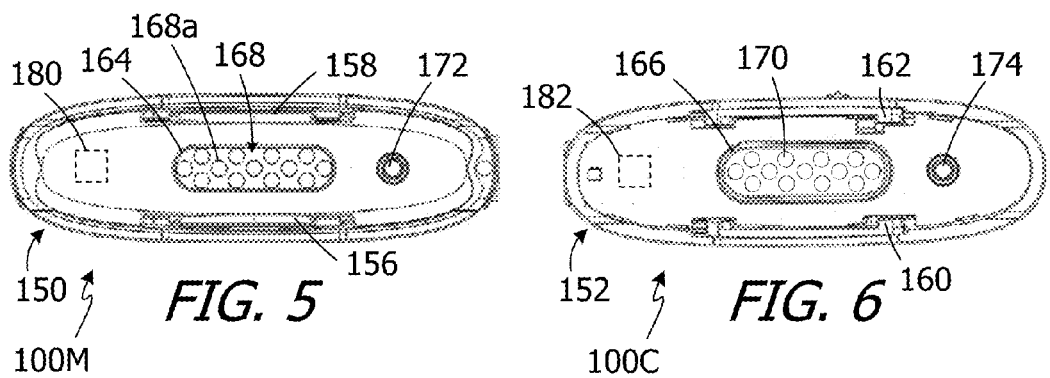
FIG. 5 is a plan view of a sound processor main portion in accordance with one embodiment of a present invention.
FIG. 6 is a plan view of a sound processor control portion in accordance with one embodiment of a present invention.

A wide variety of electrical connector arrangements may be employed. In the illustrated embodiment, the sound processor main portion 100M supplies power to the control portion 100C by way of at least some of the contacts 168 and 170 on the electrical connectors 164 and 166 (FIGS. 4-6). To that end, and referring again to FIG. 1, the sound processor main portion 100M also includes an interface controller 178 that selectively supplies power (e.g., DC power) to one or more of the contacts 168. In particular, the interface controller 178 may be configured to supply power to one or more of the contacts 168 in response to the sound processor control portion 100C (or other power consuming device) being docked to the main portion 100M, and to not supply power to the contacts 168 when there is not a control portion (or other power consuming device) docked to the main portion. One such contact is contact 168a, which is the power supply contact that powers the control portion 100C. Other contacts 168 may also be selectively connected to, and disconnected from, a voltage bias or other power source in response to docking.

The exemplary sound processor main portion 100M may be provided with a sensor that senses when the control portion 100C (or other dockable power consuming device) is docked to the main portion. The sensor supplies a signal to the interface controller 178 (FIG. 1) which indicative of the presence (or absence) of the control portion 100C (or other dockable power consuming device) and the interface controller supplies power to the appropriate electrical contacts 168 in response to the signal being indicative of the presence of a power consuming device such as the control portion 100C.

A wide variety of sensors may be employed. Referring to FIGS. 1, 5 and 6, in the illustrated implementation, the main portion 100M includes a magnetic sensor 180, such as a switch that changes state (i.e., opens or closes) when a magnet is in close proximity thereto or a device that provides digital or analog output based on the proximity of a magnet thereto, and the control portion 100C includes a magnet 182. The magnetic sensor 180 and magnet 182 may be positioned such that the magnetic field of the magnet at the magnetic sensor will only be strong enough to change the state of the sensor (or otherwise be sensed) when the control portion 100C is secured to the main portion 100M by way of the mechanical connectors 156-162 (FIGS. 5 and 6). Additionally, and although the present inventions are not so limited, the magnetic sensor 180 and magnet 182 are located inwardly of the outer surface of the housings 150 and 152, i.e., inward of or at least partially embedded in a wall of the associated housing. In other embodiments, the magnetic sensor 180 and/or magnet 182 may be carried associated with the outer surface of the housing 150 and/or 152.

Suitable magnetic sensors include, but are not limited to, magnetoresistive sensors, Hall effect sensors, and reed switches. By way of example, but not limitation, suitable magnetoresistive switches include those in the AS series of anisotropic-magneto-resistance (AMR) sensors from Murata Manufacturing Co., Ltd. (e.g., the AS-M15SA-R). Other suitable magnetic sensors include giant magnetoresistive (GMR) sensors from NVE Corporation.

There are a number of advantages associated with only supplying power to the electrical contacts 168 when the control portion 100C (or other power consuming device) is docked to the main portion 100M. For example, supplying power to the contacts 168 increases the likelihood that they will corrode in the presence of salts, water and some chemicals such as (collectively "corrosive substances") because the power supplies electromotive force that drives corrosion. In view of the fact that (1) there is no reason to supply power to the electrical contacts 168 when the main portion 100M is not connected to the control portion 100C (or other dockable power consuming device) and (2) the electrical contacts 168 are more likely to be exposed to corrosive substances when the control portion has been removed, selectively supplying power to the contacts in the manner described above reduces the likelihood of corrosion without degrading the functionality of the sound processor 100.

Figure 8:
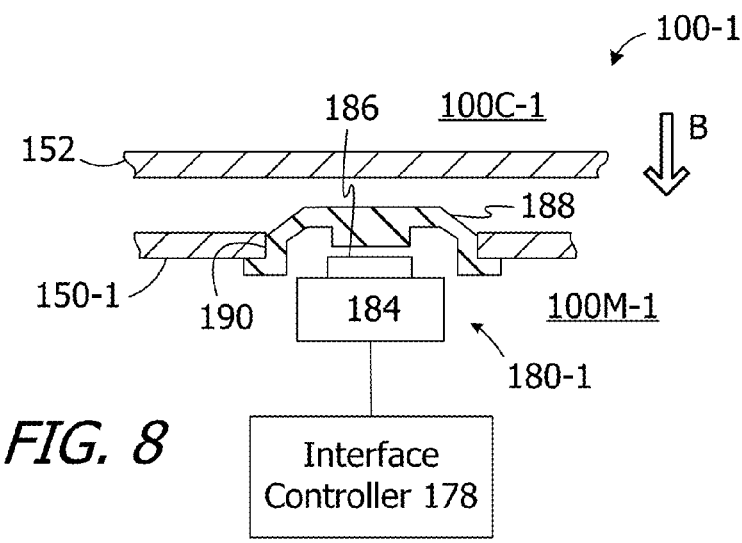
FIG. 8 is a section view of a portion of a sound processor in accordance with one embodiment of a present invention.

As alluded to above, a wide variety of sensors and sensor arrangements may be employed. By way of example, but not limitation, a mechanical switch may be employed. One example of a sound processor with such a switch is generally represented by reference numeral 100-1 in FIG. 8. Sound processor 100-1 is substantially similar to sound processor 100 and similar elements are represented by similar reference numerals. Here, however, the main portion 100M-1 includes a mechanical switch 180-1 that closes when the control portion 100C-1 moves in the direction of arrow B and reaches the docked state (see FIGS. 2 and 3). The exemplary switch 180-1 includes a fixed portion 184, a movable portion 186 and a resilient fluid-tight seal 188 that extends through an aperture 190 in the main portion housing 150-1. Here, a portion of the sensor (i.e., seal 188) protrudes beyond the outer surface of the main portion housing 150-1. In other arrangements, the control portion housing 152 may include a protrusion that depresses a switch on the sound processor main portion that is flush with the outer surface of the housing or is recessed into the housing.

Figure 9:
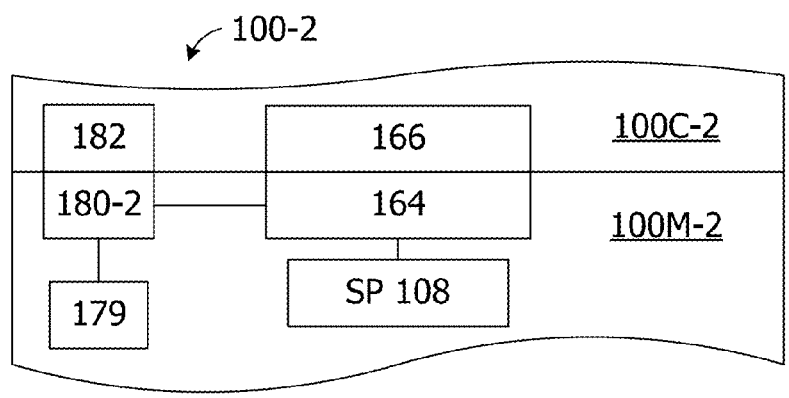
FIG. 9 is a functional block diagram of a portion of a sound processor in accordance with one embodiment of a present invention.

It should also be noted that, in those instances where a switch-type sensor is employed, such as the above-described magnetic switch and mechanical switch sensors, the switch may be in-line between a power source and the electrical contacts 168. One example of a sound processor with such a switch is generally represented by reference numeral 100-2 in FIG. 9. Sound processor 100-2 is substantially similar to sound processor 100 and similar elements are represented by similar reference numerals. For example, the main portion 100M-2 includes a magnetic switch 180-2 that is closed when the control portion 100C-2 (and magnet 182) is in the illustrated docked state. Here, however, the switch 180-2 is in-line between the power source 179 (e.g., an internal voltage regulator, or an unregulated power supply such as the power source 124 directly or a power supply that is derived from the power source 124) that supplies power to the appropriate electrical contacts 168 of the connector 164. The electrical contacts are, therefore, connected to the power source when the switch 180-2 is closed and disconnected from the power source when the switch is open.

In other implementations, and regardless of the type of sensors employed, sound processors may be configured such that a number of different devices can be docked to the main portion. For example, more than one sensor may be provided on the sound processor main portion so that the sound processor main portion can distinguish between the above-described control portion 100C and other devices that may be docked to the main portion.

Figure 10B:
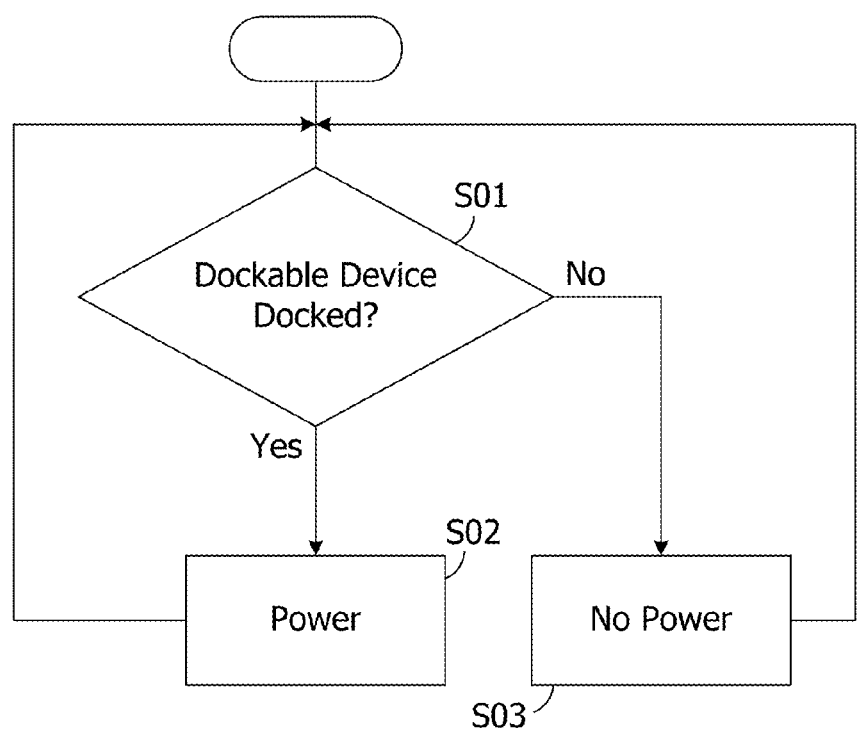
FIG. 10B is a flow chart in accordance with one embodiment of a present invention.

One example of a sound processor that employs various dockable devices in addition to a dockable control portion is generally represented by reference numeral 100-3 in FIG. 10. Sound processor 100-3 is substantially similar to sound processor 100 and similar elements are represented by similar reference numerals. Here, however, the main portion 100M-3 includes a second sensor 181 that is connected to the interface controller 178 (FIG. 1), and the sound processor 100-3 may be configured to be operatively combined with two alternate (or "auxiliary") dockable devices 100C-3 and 100C-3', in addition to the control portion 100C, that may be docked to the main portion. One, both or none of the alternate dockable devices 100C-3 and 100C-3' may be power consuming devices. For example, the devices 100C-3 and 100C-3' may be any two of a radio receiver, WiFi receiver, Bluetooth® receiver, IEEE 802.11 receiver, assistive listening device, other wireless devices or other suitable devices that may be operatively connected to the sound processor circuitry 108 or other aspect of the main portion 100M-3. The alternate dockable devices may all have the same mechanical and electrical connection mechanisms as the control portion 100C and may be connected to the main portion 100M in the same way. For example, the alternate dockable devices may include mechanical connectors 160 and 162 and an electrical connector 166 with a plurality of electrical contacts 170 (FIG. 6). The dockable devices 100C-3 and 100C-3' may also include one or more sensed objects (e.g., magnets) so that the dockable devices can be distinguished from one another and from the control portion 100C in those instances where the sensors rely on a sensed object.

The sensors on the main portion 100M-3 may be the same type of sensor (e.g., two magnetic sensors) or may be different types of sensors (e.g. one magnetic and one mechanical), and may be located near opposite ends of the main portion housing 150 (as shown). The sensors may be located adjacent to one another, or may be located in any other suitable locations. In the exemplary embodiment illustrated in FIG. 10, the sensors 180 and 181 are magnetic sensors, alternate device 100C-3 also includes a magnet 182 and a magnet 183, while alternate device 100C-3' only includes the magnet 183.

The use of two sensors and two sensed objects allows a sound processor main portion to distinguish between four different circumstances. The operation of the sound processor may be adjusted based upon the identified circumstance. In particular, and in the exemplary context of the sound processor 100-3 illustrated in FIG. 10, the sensing of a magnet at sensor 180 and the absence of a magnet at sensor 181 is indicative of the docking of control portion 100C, the sensing of magnets at both sensors 180 and 181 is indicative of the docking of auxiliary device 100C-3, the sensing of a magnet at sensor 181 and the absence of a magnet at sensor 180 is indicative of the docking of control portion 100C-3', and the absence of magnets at both sensors 180 and 181 is indicative of nothing being docked. Should the docked device 100C, 100C-3, or 100C-3' be a device that requires power, power may be supplied by way of the appropriate contacts 168, while no power will be supplied to the contacts 168 when nothing is docked and the contacts 168 are either exposed or covered by the cover 176.

The two sensors and two sensed objects arrangement may also be employed in the exemplary context of mechanical switch type sensors. One example of such a sound processor is generally represented by reference numeral 100-4 in FIG. 10A. Sound processor 100-4 is substantially similar to sound processor 100-3 and similar elements are represented by similar reference numerals. Here, however, the sound processor main portion 100M-4 includes a pair of mechanical switches 180-1 and 181-1 that extend though housing 150-4. The control portion 100C-4 includes a housing 152-4 with a single indentation 153 that will be aligned with the switch 181-1 when the control portion is docked. As a result, when the control portion 100C-4 is docked to the main portion 100M-4, the switch 180-1 will be depressed by the control portion housing 152-4 and closed (or opened, depending on the configuration) and the switch 181-1 will not. Other dockable devices (not shown) may be provided with no indentation so that the dockable device housing will depress both switched, or with a single indentation that is aligned with switch 180-1 so that only switch 181-1 will be depressed during docking. In still other implementations, the switches may be flush with the main portion housing surface or recessed, and the dockable devices may include various protrusion arrangements.

The methods of controlling power to the electrical connectors described above are graphically summarized in FIG. 10B. Briefly, a determination is made as to whether or not a dockable device is docked to the main portion (Step S01). If the device is docked, power is supplied to the main portion electrical connector (Step S02). If not, no power is supplied (Step S03). Step S03 includes disconnecting the main portion electrical connector from power when a dockable device is undocked (or "removed").

Turning to FIG. 11, the power supply receptacle 118 in the exemplary embodiment is defined by various portions of the main portion housing 150. In particular, the main portion housing 150 has a pair of end walls 192 and 194 and a pair of side walls 196 and 198 (FIG. 21) that together define the volume, or at least a portion of the volume, in which a battery or other power supply is held. The electrical contacts 120 and 122 are carried on the end walls 192 and 194 and, in the exemplary embodiment, contact 120 is a resilient contact that is depressed as the battery or other power supply is positioned between the contacts. The resilient contact 120 presses against the battery or other power supply to hold it in place. The main portion housing 150 also has a connector 256, which is used to hold the PSR cover 154 in place as is discussed below with reference to FIGS. 19-26.

The exemplary sound processor 100 may be configured for use in or around water and, accordingly, may be configured so as to insure that the power supply receptacle 118 is waterproof. More specifically, a seal 200 may carried on the main portion housing 150 in the manner illustrated in FIG. 11. Although the present inventions are not limited to any particular seal, two exemplary seals are described below. Other seals that may be employed include, but are not limited to, seals with solid cross-sections such as solid o-ring seals.

The exemplary seal 200 is a resilient band that extends around the entire perimeter of the main portion housing 150 and contacts the entire perimeter of the inner surface of the PSR cover 154 with a relatively constant force that is sufficient to prevent ingress of liquid. Although the seal 200 is removable and replaceable, it is held in the illustrated location during use. It should also be noted that the seal 200 is compressed radially when the PSR cover 154 is moved from the detached/open state (FIG. 11) where the power supply receptacle is accessible to the attached/covered state (FIGS. 2-3) where the power supply receptacle is not accessible. Put another way, the seal 200 is compressed in a direction that is perpendicular or at least substantially perpendicular to the direction that the PSR cover 154 moves as it slides onto the main portion housing 150 and over the seal.

In at least some implementations, the configuration of the PSR cover 154 is such that it facilitates the controlled radial compression of the seal 200. To that end, and referring to FIGS. 11 and 12, the PSR cover 154 in the exemplary implementation includes side walls 202 and 204, end walls 206 and 208, a bottom wall 210 and an open end 212 opposite the bottom wall. The intersections of the side and end walls 202-208, and to some extent the side and end walls themselves, are curved. The cover walls in other implementations may define a rectangular shape with 90 degree corners. The exemplary PSR cover 154 also includes an inner surface 214, with a tapered transition portion 216 and a seal portion 218, that extends completely around the perimeter of the cover. The circumference of the inner surface 214 is greatest at the open end 212, then decreases through the transition portion 216 such that the slope is about 1.0 to about 1.7, and then is substantially constant in the seal portion 218. The transition portion 216 and seal portion 218 cooperate with the seal 200 in the manner described below with reference to FIG. 16.

As illustrated in FIGS. 13 and 14, the exemplary seal 200 includes a base member 220, which defines the inner surface 222 of the seal, and a plurality of protrusions 224-228 that extend outwardly from the base member and have longitudinal ends 224a-228a. The seal 200 is formed from resilient material and, as is illustrated in FIG. 13, defines a closed geometric overall shape (e.g. circular or the illustrated oval). The seal 200 is slightly smaller than the portion of the main portion housing 150 on which is it is to be supported. As a result, the seal 200 will be pre-stressed when placed on the housing to prevent ingress of liquid between the seal inner surface 222 and the housing. The exemplary seal 200 also includes material-free regions 230 and 232 that are respectively located between protrusions 224 and 226 and protrusions 226 and 228. The material free regions 230 and 232 provide open spaces (or "air gaps") into which portion of the seal deflects during the slide-on radial compression that occurs when the PSR cover 154 is secured to the main portion housing 150. Although the protrusions 224-228 are generally planar structures that extend radially outwardly and are perpendicular to the base member inner surface 222 in the illustrated embodiment, other configurations may be employed.

Figure 15:
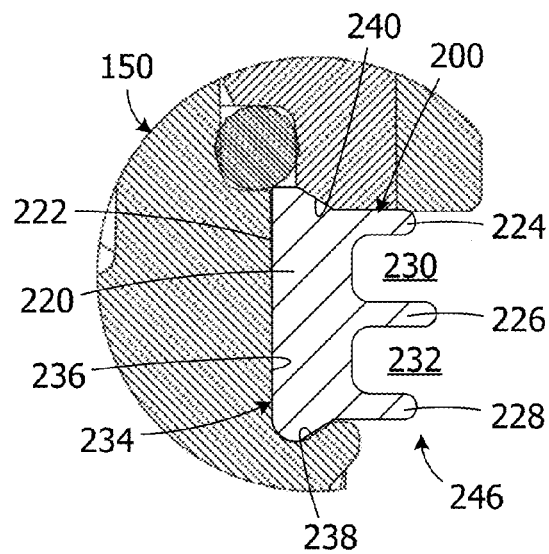
FIG. 15 is a section view of a portion of a sound processor main portion in accordance with one embodiment of a present invention with the power supply receptacle cover removed.
Figure 16:
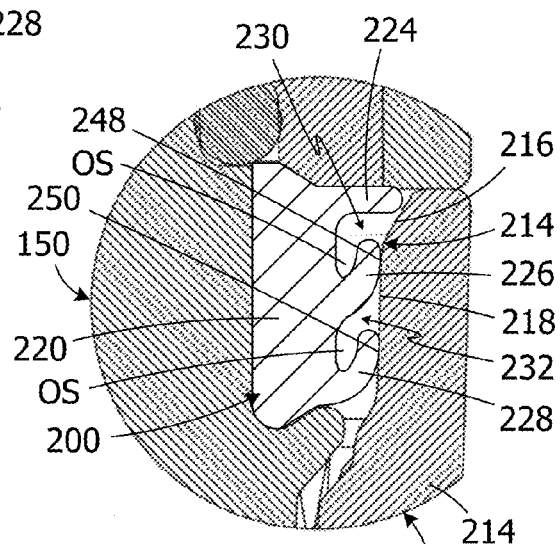
FIG. 16 is a section view of a portion of a sound processor main portion in accordance with one embodiment of a present invention with the power supply receptacle cover in place.

Turning to FIGS. 15 and 16, the exemplary main portion housing 150 has a channel 234 into which the seal 200 may be inserted. The channel 234 has an inner surface 236 that abuts the seal inner surface 204. The channel 234 also has a pair of inwardly projecting surfaces 238 and 240. The seal main portion 220 has corresponding surfaces 242 and 244 (FIG. 14). The seal 200 is stretched and deflected into the channel 234 during assembly and held in the channel 234 by the inwardly projecting surfaces 238 and 240. So arranged, the protrusions 224-228 will extend radially outwardly from the main portion 220 and one or more of the protrusions will be located within a region 246 that will ultimately be occupied by a portion of the PSR cover 154. As the PSR cover 154 in the exemplary implementation moves through the region 246, the inner surface transition portion 216 will sequentially engage and deflect the protrusions 228 and 226. When the PSR cover 154 reaches attached/covered state, which is illustrated in FIG. 16, the protrusions 226 and 228 will be deflected in the manner shown such that they engage the inner surface seal portion 218 at contact points 248 and 250 and there are open spaces OS between the protrusions and the main portion 220. Each contact point 248 and 250, which are the points at which radial force is applied to the seal 200, extends around the perimeter of the PSR cover 154 with enough force to prevent ingress of fluid.

Figure 17:
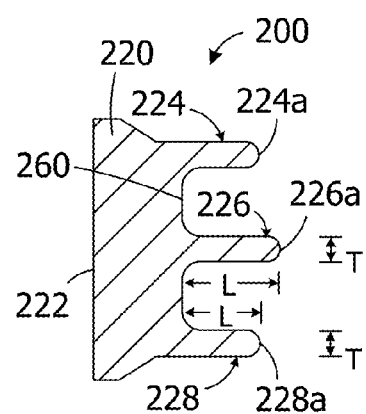
FIG. 17 is a section view of a seal in accordance with one embodiment of a present invention.

Although the protrusions 224-228 may be identical in some implementations, the protrusion 226 in the exemplary seal 200 is configured so as to have different structural characteristics than the protrusions 224 and 228. The differences in structural characteristics are differences that result in differences in sealing characteristics generally, and the creation of more sealing force at protrusion 226 in particular. Referring to FIG. 17, in the exemplary seal 200, the length L of the protrusion 226 is greater than the length of protrusion 228, while the thicknesses T of protrusions 226 and 208 are same. Given the fact that the distance between the seal base member 220 and the seal portion 218 of the PSR cover inner surface 214 is essentially the same at each protrusion, the protrusion 226 will undergo a greater degree of deflection and radial compression than the protrusion 228 because it is longer. As such, as despite the fact that the protrusions are the same thickness and formed from the same materials, the protrusion 226 will form a tighter seal than the protrusion 228 and will act as the primary portion of the seal. Locating the primary portion of the seal sufficiently away from the open end 212 is advantageous for insuring that the seal makes uniform radial contact with the PSR cover inner surface 214. The protrusion 228 functions as the secondary portion of the seal to prevent ingress of liquid should liquid pass the seal formed by protrusion 226. Such liquid will be at a lower pressure than liquid at the seal formed by protrusion 226.

It should be noted here that, given the respective dimensions of the protrusion 224 and the inner surface transition portion 216, the protrusion 224 does not create a seal or at least any substantial seal. The protrusion 224 may, therefore, be omitted in some embodiments. The protrusion 224, which is identical to protrusion 228, is included in the exemplary seal 200 for a number of other reasons. Most notably, the inclusion of the protrusion 224 makes the seal 200 symmetric about the protrusion 226 and, accordingly, it is reversible. If the seal 200 is mounted "upside down" on the housing 106, there will be no change in function and, in some instances, the life of the seal may be extended if it is removed and reversed after some period of use. The beam strength of the seal 200, as defined by the material thickness in the radial direction, is symmetric in the axial dimension. The additional beam strength associated with the protrusion 224 also improves the seal between the inner surface 222 and the inner surface 236 of the housing channel 234 created by the pre-stressing of the seal.

There are a variety of other ways to create protrusions with differing sealing characteristics. By way of example, but not limitation, differences in the respective thicknesses of the protrusions and/or materials used to form the protrusions may be employed alone or in combination with differences in other structural characteristics (e.g. length) to create protrusions having the desired differences in sealing characteristics.

Figure 18:
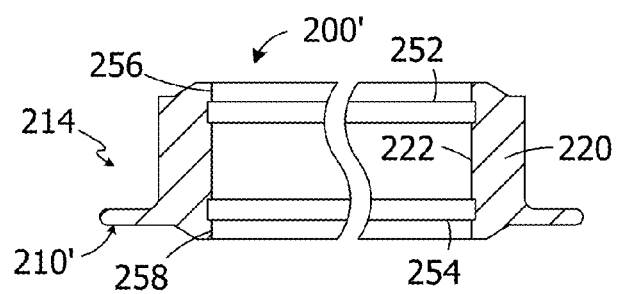
FIG. 18 is a section view of a seal in accordance with one embodiment of a present invention.
Figure 29:
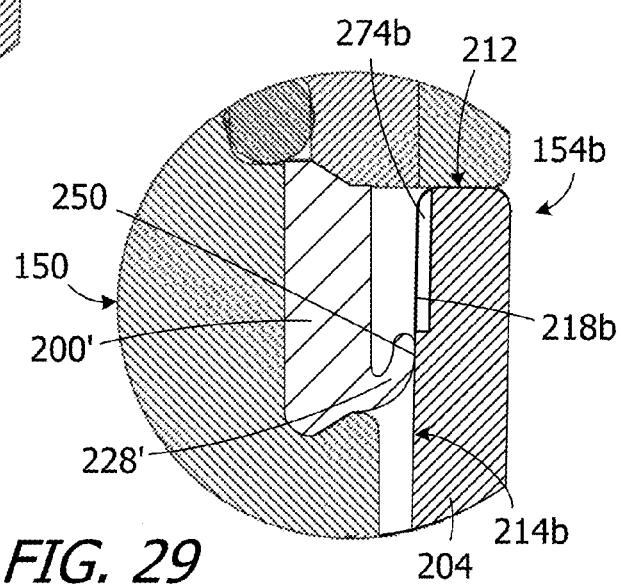
FIG. 29 is a section view of a portion of a sound processor main portion with the power supply receptacle cover in place.

Another exemplary seal, which is generally represented by reference numeral 200' in FIG. 18, and which is otherwise identical to seal 200, includes only a single protrusion 228', a single material free region 232, and one or more grooves, e.g. grooves 252 and 254, that are formed in the base member 220. The single protrusion 228' forms a seal in the manner described above in the context of protrusion 226 (FIGS. 15-16) and, in the illustrated embodiment, the single protrusion is the same length as the protrusion 226. In embodiments that include the seal 200', the inner surface of the associated PSR cover may include a tapered transition portion (e.g. transition portion 216 in FIG. 16), or as is illustrated in FIG. 29, the tapered transition portion may be omitted.

The grooves 252 and 254 are relatively shallow (e.g. about 0.004 inch), extend around the perimeter of the inner surface 222, and define relatively small (as compared to the entire surface 222) upper and lower contact surfaces 256 and 258 at the axial ends of the base member 220. The separate seals between the inner surface 222 and the inner surface 236 of the housing channel 234 formed at the spaced contact surfaces 256 and 258 are, in some instances, more readily controllable than a single seal formed from an inner surface without grooves. Although the exemplary grooves 256 and 258 are rectangular in shape, grooves of other shapes may be employed. It should also be noted that grooves, such as grooves 256 and 258, may be added to the inner surfaces of each of the other seal embodiments described above and below if so desired.

With respect to materials, suitable resilient materials for the exemplary seals disclosed herein include but are not limited to silicone. The dimensions of the seals will depend on the desired characteristics and the dimensions of the main portion housing and PSR cover, and the present seals are not limited to any particular dimensions unless such dimension are set forth in the claims below. Referring to FIG. 13, the unstretched major and minor dimensions (measured perpendicular to the Axis A) of the exemplary seal 186 are about 53.00 mm to 57.00 mm and about 14.00 mm to 16.00 mm. Turning to FIG. 17, the thickness of the base member 220, i.e. the distance between inner surface 222 and outer surface 260, is about 0.90 mm to 1.00 mm, the height of the base member is about 2.80 mm to 3.80 mm, the protrusions 224-228 are about 0.30 mm to 0.50 mm thick, the protrusions 224 and 228 are about 0.80 mm to 1.00 mm long, and the length of protrusion 226 is about 1.0 mm to 1.20 mm.

The PSR cover and seal arrangements described above in the context of the illustrated embodiments are such that the waterproof rating at the PSR cover will be IPX7, i.e. there will be no ingress of visible water into the power supply receptacle 118 when the exemplary sound processor 100 is immersed in water at a depth of 1 meter for 30 minutes.

The exemplary sound processor 100 may also include a connector apparatus that secures the PSR cover 154 to the main portion housing 150. One example of such a connector apparatus is illustrated in FIGS. 19-22. Additionally, or alternatively, the sound processor 100 may be configured so as to insure that the PSR cover 154 must be gripped in a particular way to facilitate removal, as discussed in greater detail below with reference to FIGS. 23-26.

As illustrated for example in FIGS. 19-22, the exemplary connector apparatus 256 (FIG. 22) includes protrusions 258 and 260, which are carried by the PSR cover walls 202 and 204, and are configured to mate with indentations 262 and 264 in the side walls 196 and 198 of main portion housing 150. Each of the protrusions 258 and 260 includes two cam surfaces 266 and 268 (FIG. 22), and each of the side walls 196 and 198 includes edges 270 (FIGS. 21-22). The resilience of the PSR cover 154 allows the side walls 202 and 204 to deflect as the cover moves from the detached/open state (FIGS. 19-20) to the attached/covered state (FIGS. 21-22) and from the attached/covered state to the detached/open state. More specifically, as the PSR cover 154 moves from the detached/open state toward the main portion housing 150, the cam surfaces 268 on the cover protrusions 258 and 260 will engage the edges 270 of housing walls 196 and 198. As the PSR cover 154 continues to move in this direction, the cover walls 202 and 204 will deflect radially outwardly, as permitted by the resilience of the PSR cover 154, while the protrusions 258 and 260 pass the edges 270. The PSR cover walls 202 and 204 will remain deflected radially outwardly until the protrusions 258 and 260 are aligned with the indentations 262 and 264. At this point, the resilience of the PSR cover 154 will cause the walls 202 and 204 to move radially inwardly such that the protrusions 258 and 260 are located within the indentations 262 and 264, in their radially retracted positions, thereby locking the cover in place. Conversely, when the PSR cover 154 pulled in the opposite direction, the cam surfaces 266 on the protrusions 258 and 260 will engage the edges 272 of the side walls 196 and 198. The cover walls 202 and 204 will deflect radially outwardly, to their radially extended positions, and the protrusions 258 and 260 will move out of the indentations 262 and 264 as the PSR cover 154 continues to be pulled away from the main portion housings 150.

The protrusions 258 and 260 and indentations 262 and 264 in the illustrated embodiment are also elongate and located at the longitudinally central region of the housing side walls 196 and 198 and PSR cover side walls 202 and 204. The longitudinally central region of the PSR cover side walls 202 and 204 is the region of maximum radial extension.

Suitable resilient materials for the PSR cover 154 include, but are not limited to, a polycarbonate (PC)/acrylonitrile butadiene styrene (ABS) resin. Such materials, in combination with a wall thickness of about 0.050 inch and the other dimension of the cover described herein will allow the PSR cover 154 to resiliently deflect in the manner described above.

The main portion 150 and control portion 152 of the exemplary housing 106 may be formed from materials including, but not limited to, PCs, ABSs, PC/ABS blends, nylon and various combinations thereof. One specific example is Lexan® Resin HP1R, from SABIC Innovative Plastics Company. Another specific example is Noryl® PPO, a modified polyphenylene oxide. In one exemplary implementation, the main portion 150 may include a main structure formed from Lexan® Resin HP1R and a decorative overmold formed from a platable grade of PC/ABS with a chrome plating on the PC/ABS. In other implementations, the housing main portion 150 and control portion 152 may be formed from the same materials as the PSR cover 154, but will be stiffer due to the geometry.

It should be emphasized here that the connector apparatus 256 is merely one example of an apparatus that may be carried on the cover side walls 202 and/or 204 and used to secure the PSR cover 154 to the main portion housing 150. By way of example, but not limitation, an alternative PSR cover and main portion housing arrangement may be configured such that the locations of the above-described protrusions, indentations, cam surfaces and edges are reversed. Another alternative is to simply include a protrusion and indentation, along with the associated cam surfaces and edges, on one of the cover side walls 202 and 204. A connector apparatus similar to connector apparatus 256 may also be associated with the portion of the housing above (in the illustrated orientation) the seal and with the open end of the PSR cover, i.e. located on the other side of the seal. The protrusions and indentations may also have curved surfaces instead of the linear surfaces.

The overall configuration of the housing 106 may, in some implementations, be such that the PSR cover 154 is a child resistant cover. In particular, the dimensions of the housing 106 and the location of the connector apparatus (e.g. the protrusions 258 and 260 and the indentations 262 and 264) make it exceedingly difficult for a young child (e.g. infants and toddlers up to about 4 years of age) to remove the PSR cover 154.

Referring to FIGS. 23-26, and although the present inventions are not limited to such a configuration, the length L of the housing 106 in the illustrated embodiment is substantially greater than, e.g. at least about two times and in some instances at least about three times, the width W of the housing. The length L of the exemplary housing 106 is also relatively large. The "length" is the major dimension perpendicular to the axis A which, in the illustrated embodiment, is also perpendicular to direction of cover movement (note arrows B in FIG. 23). As used herein, "relatively large" means at least 2 inches, which is a length that a young child would find difficult to grip with sufficient force to remove the PSR cover 154. Exemplary values of the length L range from about 2 inches to about 4 inches, depending on the age of the child, and the illustrated embodiment is 2.3 inches long. The width W of the exemplary housing 106 is relatively small. The "width" is the minor dimension perpendicular to the axis A which, in the illustrated embodiment, is also to the direction of cover movement (note arrows E in FIG. 24). As used herein, "relatively small" means no more than 2 inches (e.g. when the length is 4 inches). Exemplary values of the width W range from about 0.25 inch to about 2 inches, and the illustrated embodiment is about 0.7 inches wide. The lengths of the main portion housing side walls 196 and 198 and the PSR cover side walls 202 and 204 closely correspond to, or are the same as, the length L of the housing 106, while the lengths of the main portion housing end walls 192 and 194 and the PSR cover end walls 206 and 208 closely correspond to, or are the same as, the width W of the housing 106. As noted above, the wall thickness of the PSR cover 154, in combination with the resiliency of the cover materials, facilitates the resilient radial deflection of the side walls 202 and 204.

Given the configuration described in the preceding paragraph, its would be extremely difficult, as well as counterintuitive, for a young child to grip the PSR cover at the end walls 192 and 194. The distance between the end walls 192 and 194 is too great to fit within a young child's hand. Instead, when attempting to pull the PSR cover 154 from the main portion housing 150, a young child will grip the PSR cover 154 at the side walls 202 and 204. The distance between side walls 202 and 204 is considerably smaller and, accordingly, they are easier to grip. A gripping force in the direction of arrows C will be applied to the side walls 202 and 204 when applying removal force in the direction of arrows B (FIG. 23). Applying gripping force in the direction of arrows C will, however, prevent the protrusions 258 and 260, which are carried by the PSR cover side walls 202 and 204 (FIG. 21), from moving out of the indentations 262 and 264. The gripping force prevents the PSR cover side walls 202 and 204 from moving radially outwardly. As the young child pulls harder in the direction of arrows B, he/she will also apply more force in the direction of arrows C to maintain a grip on the cover 154, thereby preventing the protrusions 258 and 260 from coming out of the indentations 262 and 264 despite the increase in the pulling force that would otherwise deflect the side walls 202 and 204 radially outwardly.

When an adult who is aware of the present configuration desires to remove the PSR cover 154 from the main portion housing 150, he/she will grip the cover at the end walls 206 and 208 and apply a gripping force in the direction of arrow D (FIG. 25) and removal force in the direction of arrows B (FIG. 23). The cam surfaces 266 on the protrusions 258 and 260 will engage the edges 272 of the side walls 196 and 198 as the cover 154 moves in the direction of arrows B. Because there is no gripping force preventing the cover walls 202 and 204 from deflecting radially outwardly, the protrusions 258 and 260 will move out of the indentations 262 and 264 as the PSR cover 154 moves in the direction of arrows B, thereby unlocking the cover and permitting removal.

PSR covers may also be provided with structures that facilitate movement of the PSR cover to and from the attached/covered state (FIGS. 16 and 21). More specifically, the robust seal provided by the seal 200 (or 200') may trap air within the power supply receptacle 118 as the PSR cover 154 approaches the attached/covered state during placement of the PSR cover over the power supply receptacle. The pressure of the air (if trapped) will then increase as the PSR cover 154 continues its movement to the attached/covered state, thereby creating a force that opposes the force being applied by the user. Similarly, when the user pulls the PSR cover 154 from the attached/covered state at the outset of the removal process, a suction force that is created by the trapped air will oppose removal of the PSR cover until the PSR cover has moved a distance sufficient to break the seal.

Figure 27:
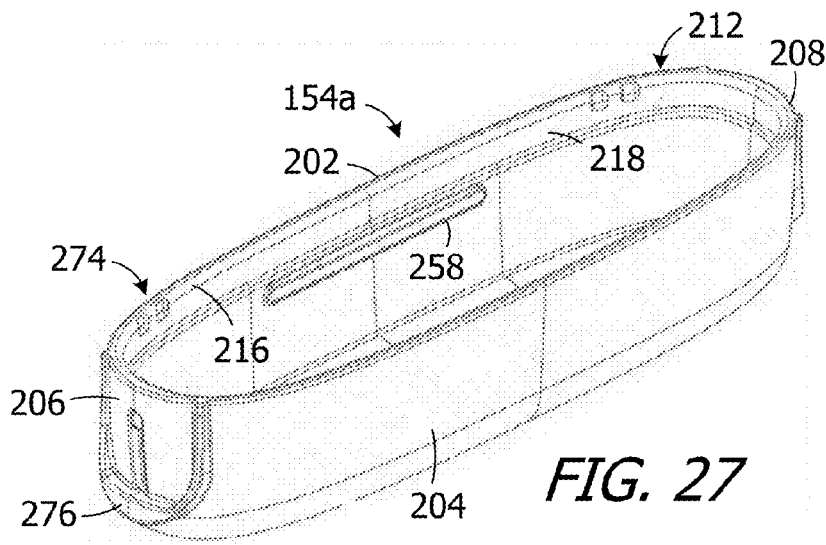
FIG. 27 is a perspective view of a power supply receptacle cover in accordance with one embodiment of a present invention.
Figure 28:
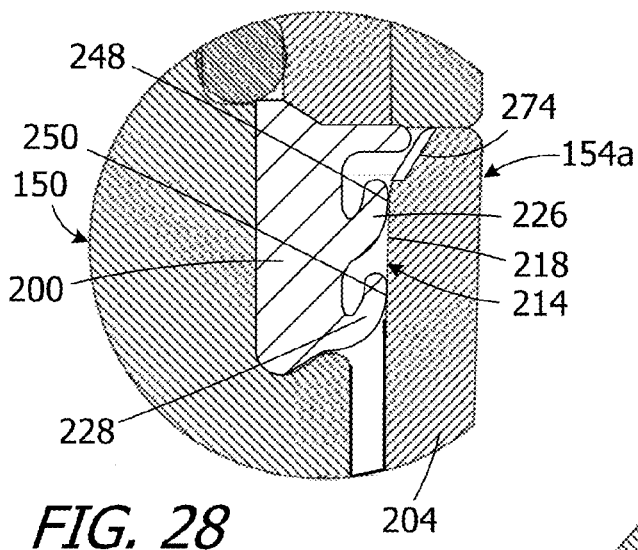
FIG. 28 is a section view of a portion of a sound processor main portion with the power supply receptacle cover illustrated in FIG. 27 in place.

One example of a PSR cover that is configured to vent air without effecting the seal provided by seal 200, and which may be incorporated into any of the sound processors described herein, is generally represented by reference numeral 154a in FIGS. 27 and 28. PSR cover 154a is essentially identical to PSR cover 154 and similar elements are represented by similar reference numerals. The PSR cover 154a also includes one or more vents. The vents may be of any suitable number, form or location. There are four sets of two vents 274 in the illustrated embodiment, with two sets on each side wall 202 and 204. The sets of vents 274 may be located at the same locations on the side walls 202 and 204, as they are in the exemplary embodiment, or may be at different locations.

In the illustrated embodiment, the vents 274 are located in the tapered transition portion 216 and, accordingly, do not effect the seal formed between the cover inner surface seal portion 218 and the seal protrusion 226 (FIG. 28) at contact point 248. However, during placement of the PSR cover 154a onto the housing main portion 150, the vents 274 permit air passage past the seal protrusion 226 and prevent the aforementioned pressure increase within the power supply receptacle 118. Similarly, after the PSR cover 154a has been moved a small distance from the attached/covered state during cover removal, the vents 274 will be aligned with the seal protrusion 226 so that air can be drawn into the power supply receptacle 118, thereby preventing the creation of suction force.

It should also be noted that the vents 274 are located near both longitudinal ends of each of the cover side walls 202 and 204 in the illustrated embodiment. Thus, should the PSR cover 154a be tilted relative to housing main portion 150 when the being placed on the main portion, i.e. should one of the end walls 206 and 208 be closer to the main portion than the other, venting will occur at the trailing vents 274 as the PSR cover straightens out prior to reaching the attached/covered state. Similarly, venting will occur if the user pulls from one end of the PSR cover 154a during removal. Venting will occur at all vents 274 during placement and removal when the PSR cover 154a is not tilted relative to the housing main portion 150.

The exemplary cover 154b illustrated in FIG. 29 is essentially identical to PSR cover 154a and similar elements are represented by similar reference numerals. Here, however, the cover 154b is configured for use with seal 200'. To that end, the cover includes an inner surface 214b without a tapered transition portion. The seal portion 218 extends essentially to the open end 212. The single protrusion 228' forms a seal at contact point 250.

To facilitate movement of the PSR cover 154b to and from the attached/covered state, the PSR cover also includes vents 274b that may be of any suitable number, form or location. There may be four sets of two vents 274b, as is described above with reference to vents 274, with the vents being long enough to extend from about the open end 212 to the illustrated location adjacent to the contact point 250.

The exemplary PSR cover 154a illustrated in FIGS. 27 and 28 also includes a protrusion 276 on the cover end walls 206 and 208. The protrusions 276, which help the user grip the end walls 206 and 208, may also be employed on the PSR covers 154 and 154b.

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A sound processor, comprising:
a dockable device, which does not include sound processor circuitry, including at least one dockable device electrical contact; and
a main portion including a housing defining an exterior, sound processor circuitry, means for connecting the sound processor circuitry to a cochlear implant headpiece, at least one main portion electrical contact associated with the housing exterior, and a control apparatus configured to determine when the dockable device is and is not docked to the main portion and to supply power to the at least one main portion electrical contact when the dockable device is docked to the main portion and to not supply power to the at least one main portion electrical contact when the dockable device is not docked to the main portion.

2. A sound processor as claimed in as claimed in claim 1, wherein the control apparatus includes a sensor.

3. A sound processor as claimed in claim 2, wherein
the sensor comprises a magnetic sensor; and
the dockable device includes a magnet.

4. A sound processor as claimed in claim 3, wherein
the magnetic sensor comprises a switch that is configured to change state when the dockable device is docked to the main portion.

5. A sound processor as claimed in claim 2, wherein the sensor comprises a mechanical switch.

6. A sound processor as claimed in claim 1, wherein the dockable device includes a user manipulatable control device.

7. A sound processor as claimed in claim 1, wherein the main portion and the dockable device include respective mechanical connectors that secure the main portion and dockable device to one another.

8. A sound processor, comprising
a first dockable device including at least one dockable device electrical contact;
a second dockable device; and
a main portion including a housing defining an exterior, sound processor circuitry, means for connecting the sound processor circuitry to a cochlear implant headpiece, at least one main portion electrical contact associated with the housing exterior, and a control apparatus configured to supply power to the at least one main portion electrical contact when the first dockable device is docked to the main portion, to not supply power to the at least one main portion electrical contact when the first dockable device is not docked to the main portion and to distinguish between the first and second dockable devices.

9. A sound processor as claimed in claim 8, wherein the control apparatus includes first and second sensors.

10. A sound processor as claimed in claim 9, wherein
the main portion defines first and second longitudinal ends; and
the first and second sensors are respectively associated with the first and second longitudinal ends.

11. A method of controlling a sound processor including a main portion with a housing, a main portion electrical connector, sound processor circuitry within the housing and a headpiece port on the housing that receives a pulse sequence from the sound processor circuitry, and a dockable device with a dockable device electrical connector and a user-manipulatable volume control element, the method comprising the steps of:

connecting the main portion electrical connector to a source of electrical power solely in response to the dockable device being docked to the main portion;

supplying the pulse sequence from the sound processor circuitry within the main portion housing to a headpiece connected to the headpiece port on the main portion housing;

adjusting volume defined by the pulse sequence supplied by the sound processor within the main portion housing in response to manipulation of the volume control element on the dockable device; and disconnecting the main portion electrical connector from the source of electrical power solely in response to the dockable device being undocked from the main portion.

12. A method as claimed in claim 11, further comprising the step of:

sensing whether the dockable device is docked to the main portion or is undocked from the main portion.

13. A method as claimed in claim 11, further comprising the step of:

sensing whether the dockable device is docked to the main portion or is undocked from the main portion with a switch.

14. A method as claimed in claim 11, further comprising the step of:

sensing whether the dockable device is docked to the main portion or is undocked from the main portion with a magnetic switch.

15. A sound processor, comprising:

a dockable device, which does not include a power source, including at least one dockable device electrical contact and a control panel that has a user-manipulatable control device;

a main portion including a housing defining an exterior, sound processor circuitry controlled by the user-manipulatable control device, and at least one main portion electrical contact associated with the housing exterior;

a power source associated with the main portion;

means for determining when the dockable device is and is not docked to the main portion; and means for connecting the at least one main portion electrical contact to the power source when the dockable device is docked to the main portion and disconnecting the at least one main portion electrical contact from the power source when the dockable device is not docked to the main portion.

16. A sound processor as claimed in claim 15, wherein the main portion and the dockable device include respective mechanical connectors that secure the main portion and dockable device to one another.

17. A sound processor as claimed in claim 15, wherein the user-manipulatable control element comprises a knob.

18. A sound processor as claimed in claim 15, wherein the user-manipulatable control element comprises a switch.

19. A sound processor as claimed in claim 1, wherein the main portion does not include user-manipulate elements that control volume level and program selection.

20. A sound processor, comprising:

a dockable device, which does not include sound processor circuitry, including at least one dockable device electrical contact; and a main portion including a housing defining an exterior, sound processor circuitry, means for connecting the sound processor circuitry to a cochlear implant headpiece, at least one main portion electrical contact associated with the housing exterior, a power supply, and a switch that connects the power supply to the at least one main portion electrical contact when the dockable device is docked to the main portion and disconnects the power supply from the at least one main portion electrical contact when the dockable device is not docked to the main portion.

21. A sound processor as claimed in claim 20, wherein the control apparatus includes a sensor configured to determine when the dockable device is and is not docked to the main portion.

22. A sound processor as claimed in claim 20, wherein the dockable device includes a user manipulatable control device.

23. A sound processor as claimed in claim 20, wherein the main portion and the dockable device include respective mechanical connectors that secure the main portion and dockable device to one another.

\* \* \* \* \*